(12) United States Patent
Watanabe et al.

(10) Patent No.: US 7,537,385 B2
(45) Date of Patent: May 26, 2009

(54) RADIOGRAPHIC APPARATUS

(75) Inventors: Tetsuo Watanabe, Tochigi (JP); Makoto Saito, Kanagawa (JP); Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/724,171

(22) Filed: Mar. 15, 2007

(65) Prior Publication Data

US 2007/0165785 A1 Jul. 19, 2007

Related U.S. Application Data

(62) Division of application No. 11/373,181, filed on Mar. 13, 2006, which is a division of application No. 10/150,150, filed on May 20, 2002, now Pat. No. 7,104,686.

(30) Foreign Application Priority Data

May 30, 2001 (JP) ............................. 2001-162568

(51) Int. Cl.
*G03B 42/02* (2006.01)
*H05G 1/64* (2006.01)
(52) U.S. Cl. ................... 378/189; 378/98.8; 250/370.09
(58) Field of Classification Search ............... 378/98.8, 378/167, 177, 178, 180, 182, 188, 189, 208; 250/370.09
See application file for complete search history.

(56) References Cited

U.S. PATENT DOCUMENTS

| | | | |
|---|---|---|---|
| 4,258,264 A | 3/1981 | Kotera et al. ............... 250/484 |
| 4,823,372 A | 4/1989 | Svendsen ................... 378/185 |
| 4,876,706 A | 10/1989 | Tajima ....................... 378/174 |
| 4,947,423 A | 8/1990 | Watanabe ................... 379/358 |
| 5,218,284 A | 6/1993 | Burns et al. ................. 320/112 |
| 5,388,818 A | 2/1995 | Anton et al. ................ 271/209 |
| 5,414,764 A | 5/1995 | Watanabe et al. ........... 379/377 |
| 5,448,615 A | 9/1995 | Robertson ................... 378/182 |
| 5,526,420 A | 6/1996 | Watanabe et al. ........... 379/378 |
| 5,591,960 A | 1/1997 | Furukawa et al. ......... 250/208.1 |
| 5,594,774 A | 1/1997 | Schmidt ..................... 378/177 |
| 5,661,309 A | 8/1997 | Jeromin et al. ............. 250/580 |
| 5,715,292 A | 2/1998 | Sayag et al. ............... 378/98.8 |
| 5,773,839 A | 6/1998 | Krepel et al. .............. 250/580 |
| 5,920,070 A | 7/1999 | Petrick et al. ........... 250/370.09 |
| 6,059,454 A | 5/2000 | Masson ...................... 378/180 |
| 6,127,801 A | 10/2000 | Manor ........................ 320/112 |
| 6,208,708 B1 | 3/2001 | Hoheisel et al. .............. 378/37 |
| 6,232,607 B1 | 5/2001 | Huang .................... 250/370.09 |
| 6,243,276 B1 | 6/2001 | Neumann ..................... 363/53 |

(Continued)

FOREIGN PATENT DOCUMENTS

EP 0 603 709 A2 12/1993

(Continued)

*Primary Examiner*—Chih-Cheng G Kao
(74) *Attorney, Agent, or Firm*—Fitzpatrick, Cella, Harper & Scinto

(57) ABSTRACT

A radiographic apparatus includes a detection section including photoelectric conversion elements that detect radiation that has been transmitted through a subject. The apparatus has a substantially rectangular detection surface; and a housing that contains the detection section. The housing has a handle in an area along a longer side of the detection surface when viewed along a direction normal to the detection surface.

1 Claim, 8 Drawing Sheets

U.S. PATENT DOCUMENTS

| | | | |
|---|---|---|---|
| 6,362,482 B1 * | 3/2002 | Stettner et al. | 250/370.08 |
| 6,403,964 B1 | 6/2002 | Kyyhkynen | 250/370.09 |
| 6,501,829 B2 | 12/2002 | Matsumoto et al. | 378/154 |
| 6,538,413 B1 | 3/2003 | Beard et al. | 320/114 |
| 6,592,257 B1 | 7/2003 | Heidsieck et al. | 378/189 |
| 6,608,915 B2 | 8/2003 | Tsujii | 382/132 |
| 6,714,623 B2 | 3/2004 | Sako et al. | 378/98.8 |
| 6,731,783 B2 | 5/2004 | Tsujii | 382/132 |
| 7,104,686 B2 | 9/2006 | Watanabe et al. | 378/189 |

FOREIGN PATENT DOCUMENTS

| | | |
|---|---|---|
| EP | 0 642 264 A1 | 3/1995 |
| EP | 0 943 931 A2 | 3/1999 |
| EP | 1 069 439 A2 | 1/2001 |
| JP | 55-12429 | 1/1980 |
| JP | 56-11395 | 2/1981 |
| JP | 06-217206 | 8/1994 |
| JP | 08-238233 | 9/1996 |
| JP | 10-282598 | 10/1998 |
| JP | 06-342099 | 12/1999 |
| JP | 11-338079 | 12/1999 |
| JP | 2000-131500 | 5/2000 |

* cited by examiner

RADIOGRAPHIC APPARATUS

This application is a division of U.S. patent application Ser. No. 11/373,181, filed Mar. 13, 2006, which is a division of U.S. patent application Ser. No. 10/150,150, filed May 20, 2002, now U.S. Pat. No. 7,104,686. The contents of each of these applications are incorporated herein by reference.

BACKGROUND OF THE INVENTION

1. Field of the Invention

The present invention relates to a cassette-type radiographic apparatus having photoelectric conversion elements.

2. Description of the Related Art

Conventionally, radiographic systems have been widely used in the fields of industrial nondestructive detection and medical diagnosis. In such systems, radiation is emitted to a subject from a radiation generation means, and the intensity distribution of the radiation that has been transmitted through the subject is detected by radiation detection means in order to obtain the radiographic image of the subject. These systems use a method of taking a photograph with the combination of a photosensitive film and a fluorescent substance, that is, a commonly-called film/screen method. In this film/screen method, a rare-earth fluorescent substance, which emits light when radiation is emitted, is formed into sheets, which are held in close contact with both sides of a photosensitive film. Radiation, which has been transmitted through the subject, is converted into visible light by the fluorescent substance. This visible light is captured by the photosensitive film, and a latent image formed on the photosensitive film is developed by a chemical process so as to be made visible.

With advances in digital technology in recent years, a radiographic image recording/reproduction system, which uses a method of converting a radiographic image into an electrical signal, is proposed in Japanese Unexamined Patent Application Publication Nos. 55-12429 and 56-11395. In this proposed type of system, a radiographic image is converted into an electrical signal, which is subjected to image processing. The signal is reproduced as a visible image on a CRT, etc., and a high-quality radiographic image is obtained. Then, when the radiographic image is converted into an electrical signal, the intensity distribution of the radiation which has been transmitted through the subject is temporarily stored as a latent image in the store-type fluorescent substance. Thereafter, fluorescence corresponding to the latent image, which is created by irradiating exciting light such as laser light to the fluorescent substance, is photoelectrically read, and this is output as a visible image.

Furthermore, with advances in the semiconductor processing technology, a radiographic system using a semiconductor sensor has been developed. This type of system has a dynamic range which is very large compared to conventional radiographic systems using a photosensitive film, and has a practical advantage that a radiographic image which is not susceptible to variations of the amount of exposure of radiation can be obtained. Furthermore, since this type of system, unlike conventional systems that use a photosensitive film, does not require a chemical process, an output image can be obtained instantly.

Such a radiographic system using a semiconductor sensor comprises radiation generation means for irradiating a subject, radiation detection means for detecting the radiation which has been transmitted through a subject, image processing means for performing digital processing on an image signal from the radiation detection means, and display means for displaying a radiographic image. The radiation generation means comprises a plurality of photoelectric conversion elements arranged in a two-dimensional lattice shape, and is disposed in a radiographic room together with the radiation generation means.

Presently, to quickly photograph a wider range of portions of a subject, as radiation generation means, a radiographic device which is thin, lightweight, and portable, that is, a so-called "electronic cassette", has been developed. For example, as shown in FIG. 11, disposed inside a housing 2 of an electronic cassette 1 are: a fluorescent substance 3 for converting radiation into visible light; a photoelectric conversion element 4, arranged in a lattice shape, for converting visible light into electrical signals; a substrate 5 on which the photoelectric conversion element 4 is formed; a base 6 for supporting the substrate 5; a circuit substrate 7, having an electronic component 7a, for processing an electrical signal; and wiring 8 for electrically connecting the photoelectric conversion element 4 to the circuit substrate 7.

When this electronic cassette 1 is used, the operator varies the manner in which the electronic cassette 1 is disposed in accordance with the part of the subject to be photographed. For example, when the limbs of the subject are to be radiographed, the electronic cassette 1 is disposed horizontally on the floor, etc., and the portions of the subject to be photographed are placed on the top surface thereof. When the axial image of the shoulder joint of a subject S is to be radiographed, the electronic cassette 1 is held under the arm of the subject S as shown in FIG. 12, and radiation R is radiated from the opposing side (from above).

Next, referring to FIG. 15, the construction of another example of a conventional electronic cassette is described. FIG. 15 is a side sectional view of an example of a conventional electronic cassette. This electronic cassette 400 comprises: an image capturing element 451 formed of a fluorescent substance 451a for converting X rays into visible light, a plurality of photoelectric conversion elements 451b, arranged in a lattice shape, for converting the visible light into an electrical signal, and a board 451c on which the photoelectric conversion elements 451b are formed; a base 452 for supporting the board 451c; a circuit board 453 on which an electronic component 453a for processing a photoelectrically converted electrical signal is mounted; wiring 454 for electrically connecting the photoelectric conversion elements 451b to the circuit board 453; a power-supply circuit 460; power wiring 461 for supplying power to the photoelectric conversion elements 451b and the circuit board 453; and a housing 455 for these. The power-supply circuit 460 specifically comprises, for example, a combination of a battery and a DC/DC power-supply circuit, or a DC/DC power source for generating various voltages as a result of a predetermined voltage being externally supplied by a power-supply cable (not shown), etc.

When compared to a conventional photosensitive-film-built-in cassette, there is a possibility that as the weight increases, such an electronic cassette will be destroyed if it is inadvertently dropped. Therefore, it is thinkable that a handle should be mounted to the cassette for the purpose of reducing the likelihood of it being dropped, or the like.

For example, a handle mounted to a cassette which houses a storage-type fluorescent panel is disclosed in Japanese Unexamined Patent Application Publication No. 11-338079. In that patent application, a handle is provided on a side opposing the side from which the storage-type fluorescent panel is taken out, so that the cassette can be carried easily.

Furthermore, in Japanese Unexamined Patent Application Publication No. 06-342099, an electronic cassette having a handle mounted thereon so that the electronic cassette can be easily moved to an X-ray radiation position by hand is disclosed.

As described above, since the operator disposes the electronic cassette 1 horizontally on a floor, etc. or causes the electronic cassette 1 to be held under the arm of the subject, the electronic cassette 1 needs to be highly portable. Therefore, in order to improve the portability of the electronic cassette 1, in addition to the above-described known technologies, a bag-shaped electronic cassette 1' in which an arm-shaped handle 9 is pivotably mounted to holes 2a formed in both sides of the housing 2 as shown in FIG. 13, and an electronic cassette 1" in which a frame-shaped handle 10 is integrally provided on one end surface of the housing 2 as shown in FIG. 14 are thinkable.

Such electronic cassettes 1' and 1" do not pose problems when horizontally disposed on a floor, etc. However, when a specific portion of the subject is to be radiographed from a specific direction, for example, when the electronic cassettes 1' and 1" are held under the arm of the subject S as shown in, for example, FIG. 12, problems arise in that the handles 9 and 10 become obstacles to the subject S or the presence of the handles 9 and 10 makes it difficult to place the electronic cassette at a desired position. Therefore, it is preferable that the conventionally conceived electronic cassette 1 have high portability and be constructed so as not to decrease the degree of freedom of radiographing and so as not to cause the subject to feel discomfort.

The conventional examples described in the above-described publications disclose only that a handle is simply provided in a cassette so as to be suitable for carrying or moving the cassette, and do not disclose a construction in which a handle is attached to the electronic cassette by considering the specific properties of the electronic cassette. In particular, in the case of the electronic cassette, an important consideration is that there is a possibility that electronic parts, including semiconductor sensors, will be damaged by external impact.

And a consideration is that the electronic cassette has a construction in which a decrease of a signal-to-noise (S/N) ratio due to electromagnetic noise, etc., can be minimized. Also, a consideration is that the electronic cassette is convenient in that it is easy to hold, carry and position, and has convenience of radiographing, where a subject holds an electronic cassette and a radiograph is taken.

SUMMARY OF THE INVENTION

An object of the present invention is to provide a radiographic apparatus which solves the above-described problems, and which has high portability, with discomfort to a subject and decrease in the degree of freedom of radiographing being suppressed.

Another object of the present invention is to provide an electronic cassette in which a handle is appropriately contained, by considering the specific properties of the electronic cassette.

According to the present invention, the foregoing object is attained by providing a radiographic apparatus for detecting radiation that has been transmitted through a subject, including (i) a detection section including photoelectric conversion elements that detect radiation that has been transmitted through the subject and (ii) a housing which houses the detection section, having a substantially flat top surface on which the subject can be placed and in which a holding hole is formed.

According to the present invention, the foregoing object is also attained by providing a radiographic apparatus for detecting radiation that has been transmitted through a subject, including (i) a detection section including photoelectric conversion elements that detect radiation which has been transmitted through the subject and having a substantially rectangular detection surface with two opposing long sides and two opposing short sides and (ii) a housing that contains the detection section, having a handle located along a longer side of the detection surface when viewed along a direction normal to the detection surface.

Further, the foregoing objects are also attained by providing a radiographic apparatus for detecting radiation that has been transmitted through a subject, including (i) a detection section including photoelectric conversion elements that detect radiation that has been transmitted through a subject, and having a substantially rectangular detection surface with two opposing long sides and two opposing short sides, (ii) an electrical circuit section, arranged along a shorter side of the detection surface, that reads an electrical signal from the detection section, (iii) a driving circuit section, arranged along a longer side of the detection surface, that drives the detection section, and (iv) a housing that contains the detection section, the electrical circuit section, and the driving circuit section, the housing having a handle located along a longer side of the detection surface when viewed along a direction normal to the detection surface.

Further objects, features, and advantages of the present invention will become apparent from the following description of the preferred embodiments with reference to the attached drawings.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DETAILED DESCRIPTION OF THE PREFERRED EMBODIMENTS

Figure 1:
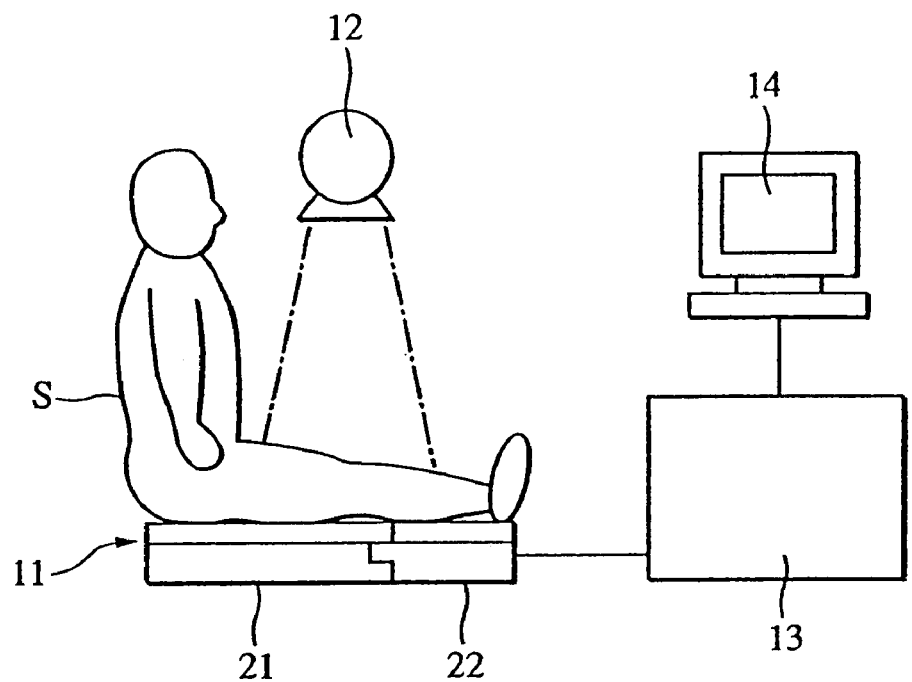
FIG. 1 shows the construction of an X-ray imaging system.

The present invention will now be described in detail with reference to the embodiments shown in FIGS. 1 to 10. FIG. 1 shows the construction of an X-ray imaging system, in which an electronic cassette 11 as an X-ray imaging apparatus of the first embodiment is horizontally disposed on a floor, etc., and an X-ray generation device 12 is disposed above the electronic cassette 11. Image processing means 13 for processing image signals is connected to the electronic cassette 11, and a monitor 14 for displaying an X-ray image is connected to the image processing means 13.

Figure 2:
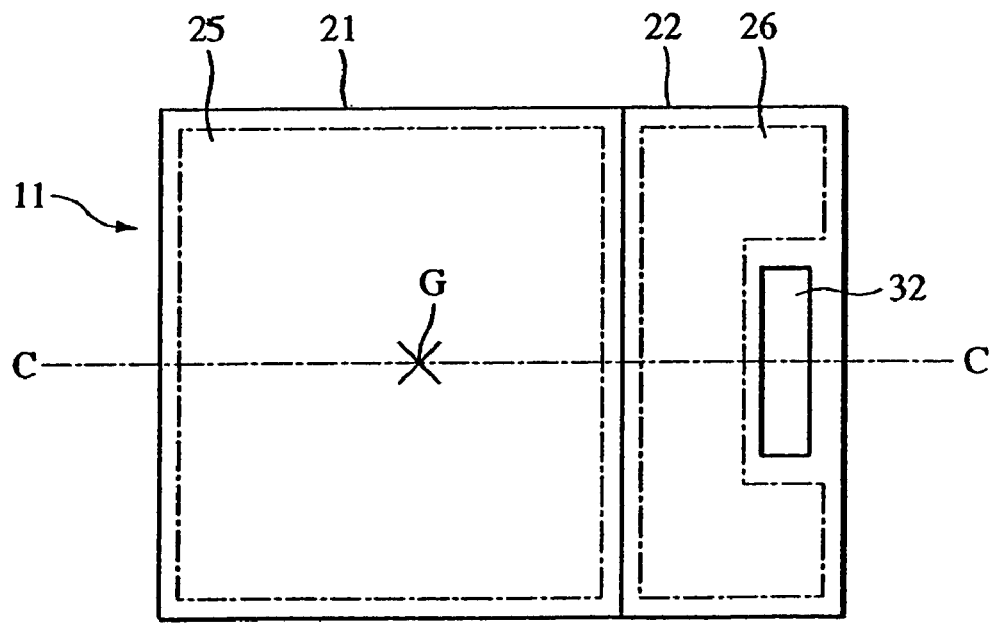
FIG. 2 is a plan view of a first embodiment of an electronic cassette according to the present invention.
Figure 3:
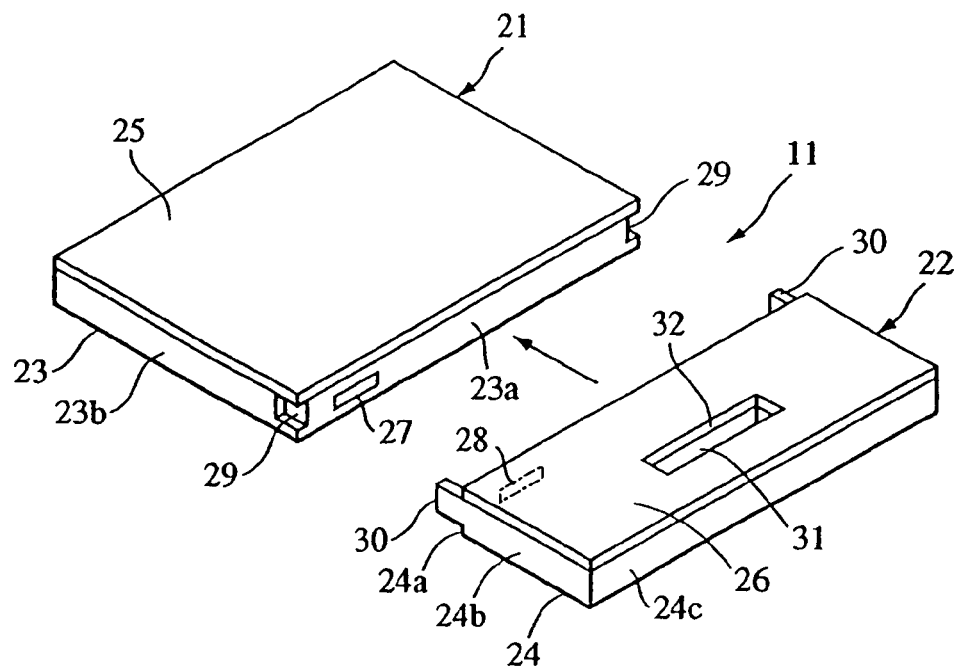
FIG. 3 is a perspective view showing a state in which a first housing and a second housing are separated from each other.

FIG. 2 is a plan view of the electronic cassette 11. FIG. 3 is an exploded perspective view of the electronic cassette 11, which can be separated/coupled, and which has a first housing 21 and a second housing 22, both of which are rectangular parallelepipeds. The housings 21 and 22 are symmetrical with respect to the center line C-C, the same in thickness with respect to the center line C-C, and the top and bottom surfaces thereof are flat without unevenness. The first housing 21 and the second housing 22 comprise first and second tray-shaped housing main units 23 and 24, and first and second lids 25 and 26 for blocking the openings of the housing main units 23 and 24, respectively. The first lid 25 of the first housing 21 is made from a material through which X rays are transmitted, and the second housing 22 is made of a metal.

The opposing surfaces 23a and 24a of the housing main units 23 and 24 are formed as rectangles of the same size, and detachable electrical connectors 27 and 28 are mounted at their opposing position, respectively. Furthermore, on side surfaces 23b and 24b of the housing main units 23 and 24, fastening sections 29 and 30, formed of, for example, a groove and a protruding piece, which are mutually fastened to each other, are provided, respectively. A holding cylindrical section 31 is formed in the vicinity of an end surface 24c of the second housing main unit 24, and a holding hole 32 which passes through to the holding cylindrical section 31 is formed in the second lid 26. The holding cylindrical section 31 and the holding hole 32 are formed in such a manner as to be rectangular when viewed in a plan view and so as to pass through to each other in the vertical direction. As FIGS. 2 and 3 show, their center is positioned along the center line C-C, and the center line C-C is formed at the center of gravity G of the electronic cassette 11 or in the vicinity thereof. More specifically, the electronic cassette 11 is constructed in such a way that the center of gravity G and the center of the holding cylindrical section 31 or the holding hole 32 are positioned substantially along the center line C-C of FIG. 2.

Figure 4:
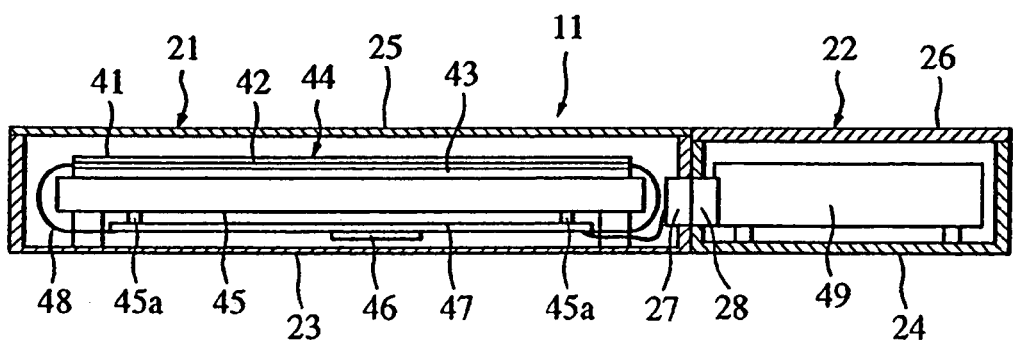
FIG. 4 is a sectional view of an electronic cassette according to the present invention.

FIG. 4 is a sectional view of the electronic cassette 11, in which, in the upper portion of the inside of the first housing 21, an X-ray detection panel 44 comprising a fluorescent plate 41, a photoelectric conversion element 42, and a board (substrate) 43 is placed on a metal base 45, and below the base 45, a circuit board 47, having an electronic component 46, for processing electrical signals, is supported. The photoelectric conversion element 42 and the circuit board 47 are connected to each other by a flexible circuit board 48, and the circuit board 47 is fixed to a projection 45a provided on the bottom surface of the base 45.

For the fluorescent plate 41, a resin plate coated with a fluorescent substance of a metal compound is used, and the fluorescent plate 41 is integrally formed with the board 43 as a result of being bonded with the board 43. For the board 43, a glass plate is often used because it is necessary that there is no chemical reaction with semiconductor elements, that it be able to withstand the temperature of semiconductor processes, and that it have dimensional stability. The photoelectric conversion element 42 is formed on the board 43 in the manner of two-dimensional arrangement by a semiconductor process.

Meanwhile, inside the second housing 22, a power source 49 for supplying power to the circuit board 47 is disposed, and the circuit board 47 is connected to the power source 49 via the electrical connectors 27 and 28. The power source 49 is formed in the shape of U in a plan view and is placed so as to surround the holding cylindrical section 31 of the second housing main unit 24.

In this first embodiment, since the first housing 21 and the second housing 22 of the electronic cassette 11 are formed as rectangular parallelepipeds and the second housing 22 is provided with the holding cylindrical section 31 and the holding hole 32 which pass through to each other, the operator can insert a finger into the holding cylindrical section 31 and the holding hole 32 in order to carry the electronic cassette 11 easily. Furthermore, since the electronic cassette 11 does not have a protruding portion, even when the electronic cassette 11 is held under the subject when, for example, the axial image of the shoulder joint is to be photographed (radiographed), the subject does not feel discomfort. In addition, since the top and bottom surfaces of the first housing 21 and the second housing 22 are flat without unevenness, even when the electronic cassette 11 is horizontally placed and the subject is made to lie on the top surfaces of the first lid 25 and the second lid 26, similarly, the subject does not feel discomfort.

Since the construction is formed in such a way that the center line C-C passing through the center of the holding cylindrical section 31 and the holding hole 32 passes through the center of gravity G of the electronic cassette 11 or the vicinity thereof, when the operator holds the electronic cassette 11, a rotational moment caused by the deviation from the center of gravity G does not act on the electronic cassette 11, and thus the operator can easily hold the electronic cassette 11. Furthermore, since the power source 49 is placed so as to surround the holding cylindrical section 31, a thin electronic cassette 11 in which a mounting space is effectively used can be realized. In addition, since the second housing 22 is made of a metal, an electromagnetic shield effect can be provided, and the penetration of electromagnetic noise which is generated from the electrical circuit of the power source 49 into the flexible circuit board 48, etc., and subsequent deterioration of the signal-to-noise (S/N) ratio can be prevented.

Although only the power source 49 is disposed in the second housing 22, the circuit board 47 or a part thereof can also be disposed. In this case, an influence due to electromagnetic noise can be greatly reduced.

Figure 5:
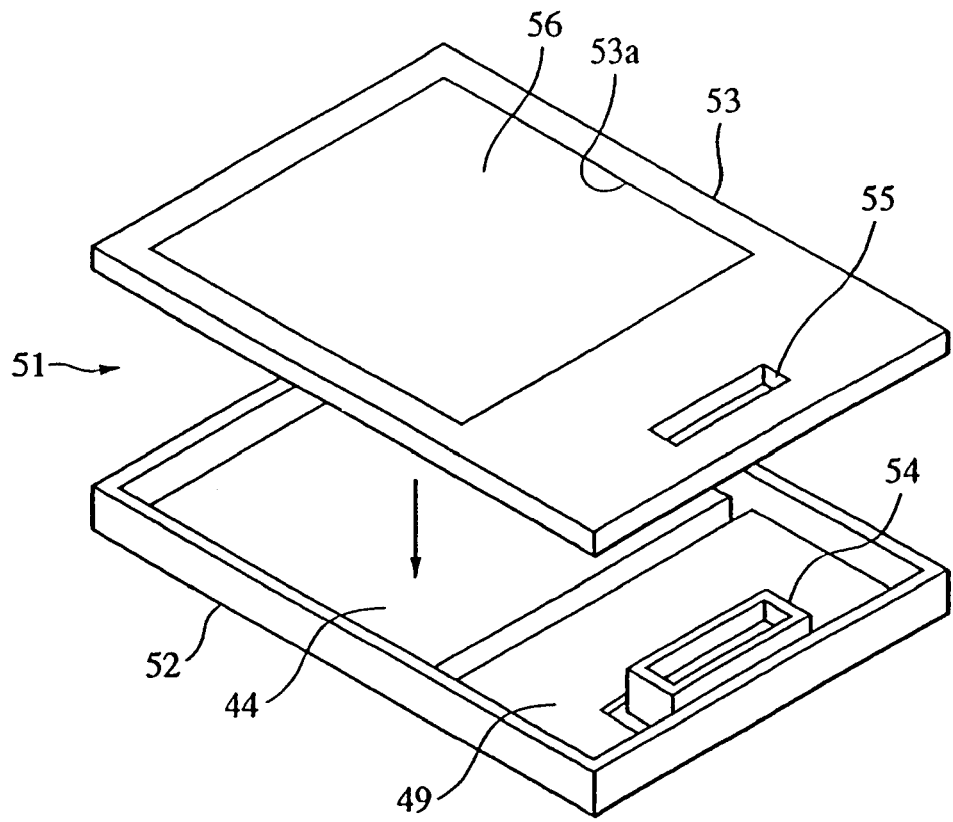
FIG. 5 is an exploded perspective view of a second embodiment of an electronic cassette according to the present invention.

FIG. 5 is an exploded perspective view of an electronic cassette of a second embodiment of the present invention. An electronic cassette 51 has a metal housing main unit 52 in a shape in which the housing main units 23 and 24 of the first embodiment are integrated, and a metal lid 53 in a shape in which the lids 25 and 26 of the first embodiment are integrated. In the housing main unit 52, a holding cylindrical section 54 having the same shape as that of the first embodiment is formed at the same position as in the first embodiment. In the lid 53, a holding hole 55 having the same shape as that of the first embodiment is formed at the same position as in the first embodiment. Inside the housing main unit 52, an X-ray detection panel 44 and a power source 49, which are the same as those of the first embodiment, are disposed. In the lid 53, an opening 53a is formed at the position opposing the X-ray detection area of the X-ray detection panel 44, and this opening 53a is blocked by a cover 56 made from carbon fiber reinforced plastics (CFRP), etc., having excellent X-ray transmittance.

In this second embodiment, the same advantages as those of the first embodiment can be achieved, and moreover, the electronic cassette 51 is formed of the integral housing main unit 52 and the integral lid 53. Consequently, resistance to bending, etc., is even greater than in the first embodiment. Furthermore, since the X-ray detection panel 44 and the power source 49 are placed inside the common housing main unit 52, the electrical circuit is more easily grounded.

Figure 6:
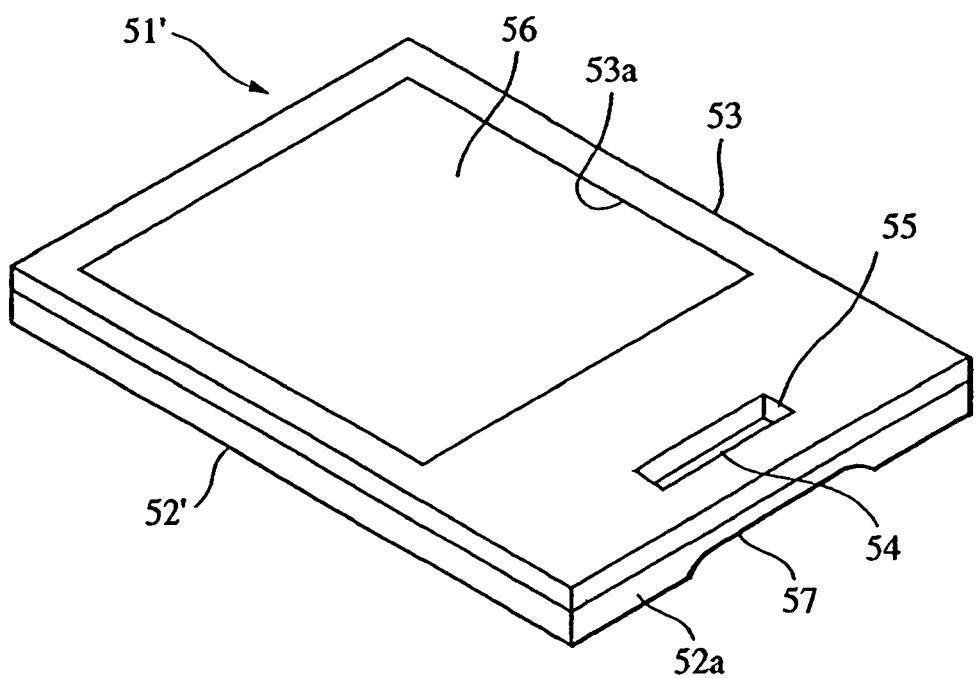
FIG. 6 is a perspective view of a third embodiment of an electronic cassette according to the present invention.

FIG. 6 is a perspective view of an electronic cassette of a third embodiment of the present invention. The electronic cassette is formed as an electronic cassette 51' which is slightly different in shape from the electronic cassette 51 of the second embodiment. In the bottom surface of a housing main unit 52', a recessed section 57, recessed in the thickness direction, which passes through to the inside of a holding cylindrical section 54 from an end surface 52a, is formed.

For the third embodiment, the same advantages as those of the second embodiment can be achieved, and moreover, portability is improved because when the operator lifts the electronic cassette 51', his/her finger can be easily hooked to the recessed section 57.

Figure 7:
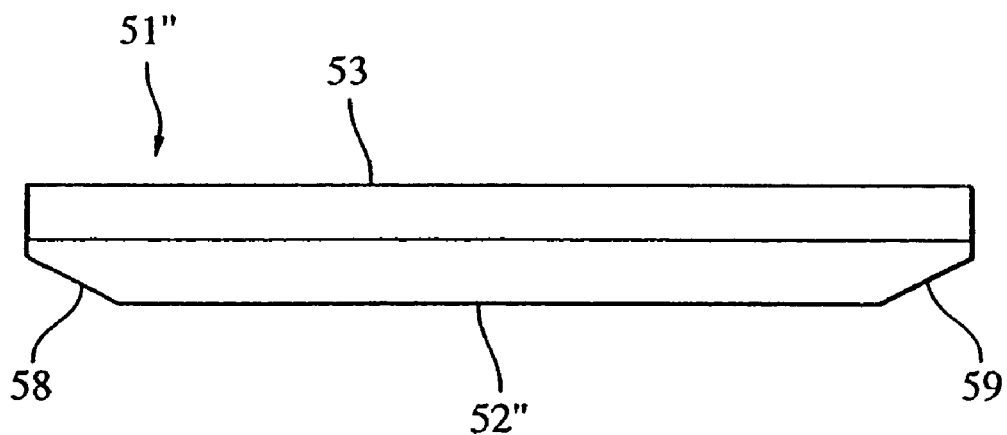
FIG. 7 is a side view of a fourth embodiment of an electronic cassette according to the present invention.

FIG. 7 is a side view of an electronic cassette of a fourth embodiment of the present invention. The electronic cassette is formed as an electronic cassette 51" which is slightly different in shape from that of the second embodiment. In particular, inclined surfaces 58 and 59 which are inclined in the thickness direction are formed on both end portions of the bottom of a housing main unit 52", respectively.

In this fourth embodiment, the same advantages as those of the second embodiment can be achieved, and moreover, portability is further improved because the operator can easily hook his/her finger to the inclined surfaces 58 and 59 of the housing main unit 52" in a horizontal state. Furthermore, since portions of both end portions of the housing main unit 52" form an obtuse angle, the housing main unit 52" softly hits the subject S, and the subject S does not feel discomfort.

In the manner described above, for the radiographic apparatus according to the first to fourth embodiments, the outer shape of the housing is substantially rectangular when viewed from the normal direction with respect to the detection surface of the detection means, and a holding hole is provided in the vicinity of one side of the outer shape. Therefore, it is possible for the operator to carry the electronic cassette with his/her finger through the holding hole, and thus the portability of the cassette is improved. Furthermore, since the outer shape of the electronic cassette does not have a protruding portion, even when the electronic cassette is held under the arm of the subject, the subject does not feel discomfort.

When the top surface of the housing including the holding hole, which is positioned on the detection surface side of the detection means, is made flat, the subject does not feel discomfort when the subject is placed on the electronic cassette in a horizontal state.

Furthermore, if the center of gravity is positioned along the center line or in the vicinity thereof, a moment does not act when the electronic cassette is held, and the portability is further improved.

In addition, when the power source is housed in the vicinity of a holding hole, the mounting space can be effectively used, and a thinner form is made possible.

Then, on one side of the housing in the vicinity of the holding hole, if the bottom surface of the housing positioned on a side opposing the detection surface is formed into a recessed shape with respect to the thickness direction, or if an inclined surface is provided with respect to the thickness direction on a surface (bottom) at a position opposing the detection surface of the detection means, the finger of the operator can be easily hooked even when the electronic cassette is placed horizontally, and the portability is further improved.

Figure 8:
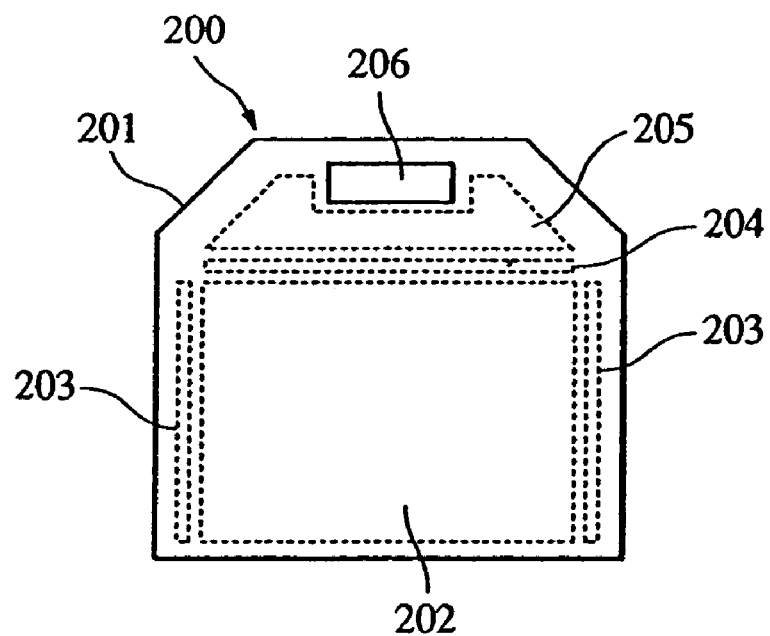
FIG. 8 is a plan view of a fifth embodiment of an electronic cassette according to the present invention.
Figure 9:
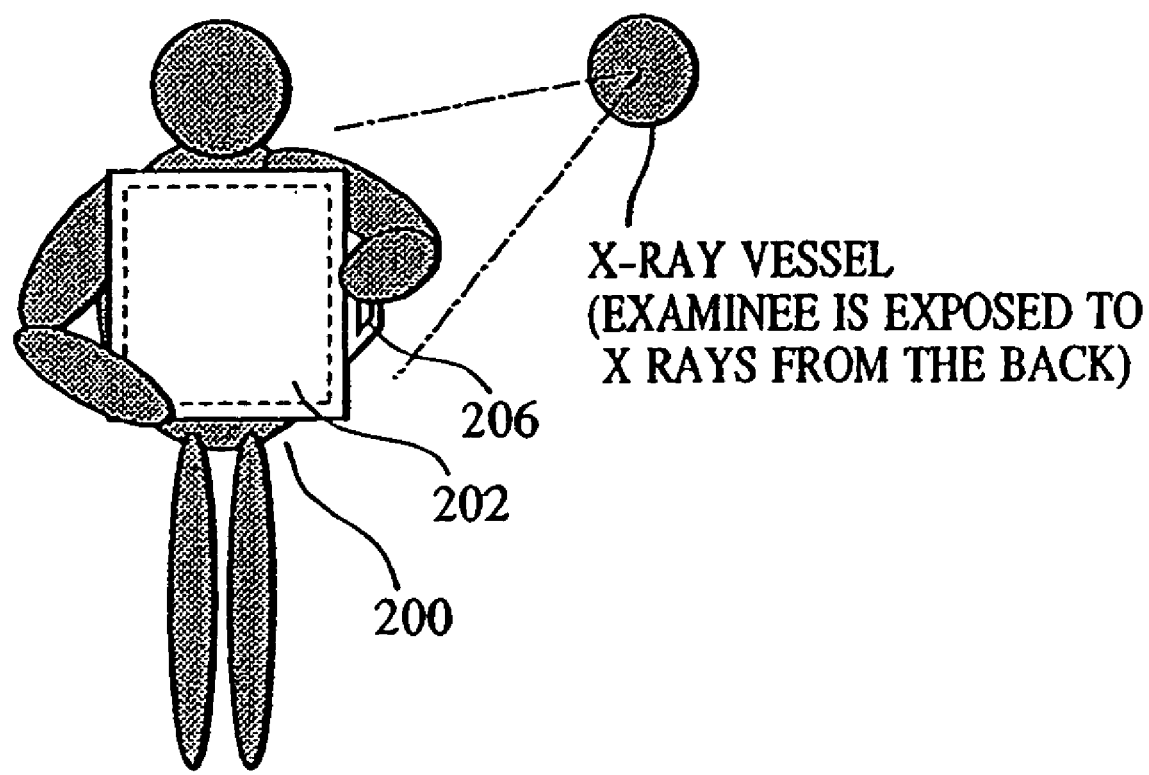
FIG. 9 is an illustration of the electronic cassette of the fifth embodiment in use.

FIG. 8 is a plan view of an electronic cassette 200 of a fifth embodiment of the present invention. A frame (housing) 201 forms the outer shape of the electronic cassette 200, and is formed of a lightweight metal or a resin. The detection surface of an X-ray detection panel (sensor section) 202 is formed rectangular, and its size is preferably, for example, 17×14 inches (43×35 cm). In the case of this size, the photograph of the chest of an adult can be taken. As another size, generally, 10×12 inches (24×30 cm), which is a size of a photosensitive film used to take a photograph of the limbs and a mammogram, may be used. The X-ray detection panel 202 is formed similarly to the X-ray detection panel 44 of the first embodiment. A circuit (to be described later) for reading electrical charge generated by photoelectric conversion is arranged, for example, from the side of the X-ray detection panel 202 to the rear thereof.

Reading of electrical charge from the X-ray detection panel is performed by a method in which the electrical charge which is generated and stored by a plurality of photoelectric conversion elements of a column selected by a driving circuit (driving circuit section) is discharged for each row and is read by an amplifier circuit (reading circuit section) placed for each row. When all data (analog signal) obtained by reading electrical charge in the row direction by the amplifier circuit is A/D-converted simultaneously, a large number of A/D converters are required. However, by providing a multiplex circuit and by performing A/D conversion by time division, the number of necessary A/D converters can be reduced. In the electronic cassette shown in FIG. 8, a driving circuit 204 for selecting a photoelectric conversion element row is disposed above the X-ray detection panel 202, and an amplifier circuit 203 for reading each electrical charge corresponding to the photoelectric conversion element row selected by the driving circuit 204 is disposed on the right and left sides of the X-ray detection panel 202.

The side of the rectangle at which a driving circuit and an amplifier circuit may be disposed so as to be adjacent to the X-ray detection panel whose detection surface is substantially rectangular may vary. However, the arrangement shown in FIG. 8 is preferable. The arrangement may vary depending on, among others, the following two points:

Factor 1: physical proximity between the driving circuit and the photoelectric conversion unit. Since delay and switch defects due to wiring resistance can become problems when selecting a row in the driving circuit, it is preferable that the driving circuit drive a photoelectric conversion element which is physically as close as possible.

Factor 2: physical proximity between the amplifier circuit and the photoelectric conversion unit. Since wiring resistance and wiring capacity can become problems when reading electrical charge in the amplifier circuit, it is preferable that the amplifier circuit read electrical charge from the photoelectric conversion element which is physically as close as possible.

First, when the arrangement of the amplifier circuit is considered on the basis of the above-described factor 2, preferably, amplifier circuits are arranged on both opposing sides as shown in FIG. 8, so that, for example, the left-side half of the X-ray detection panel is read by the amplifier circuit 203 on the left side, and the right-side half of the X-ray detection panel is read by the amplifier circuit 203 on the right side.

However, this factor does not dictate where the amplifier circuit 203 is disposed (i.e. whether on the shorter side of the X-ray detection panel 202 or on the longer side). Next, when the arrangement of the driving circuit is considered on the basis of the above-described factor 1, similarly, one column or one row is driven from both sides thereof.

Figure 12:
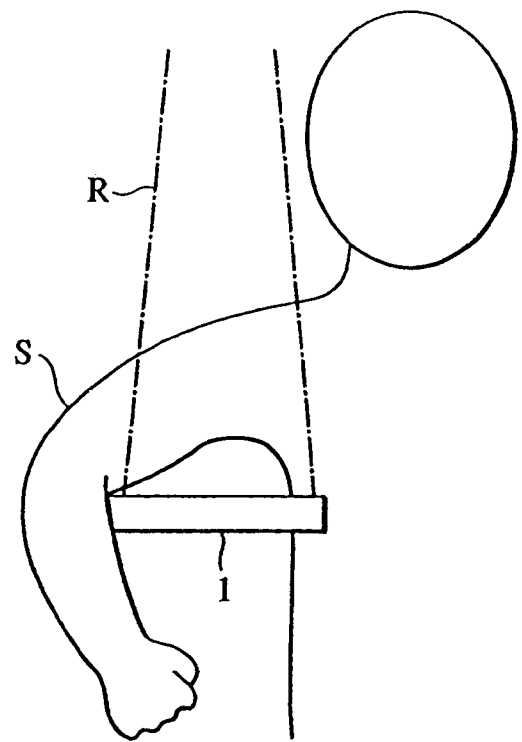
FIG. 12 is an illustration of a conventional example of an electronic cassette in use.
Figure 13:
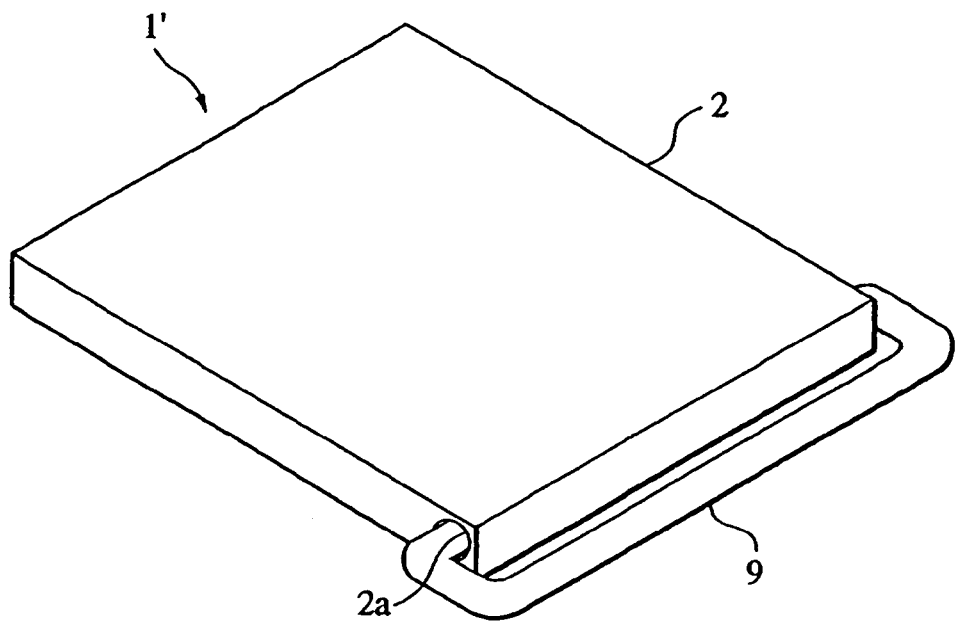
FIG. 13 is a perspective view of a conventional example of an electronic cassette.
Figure 14:
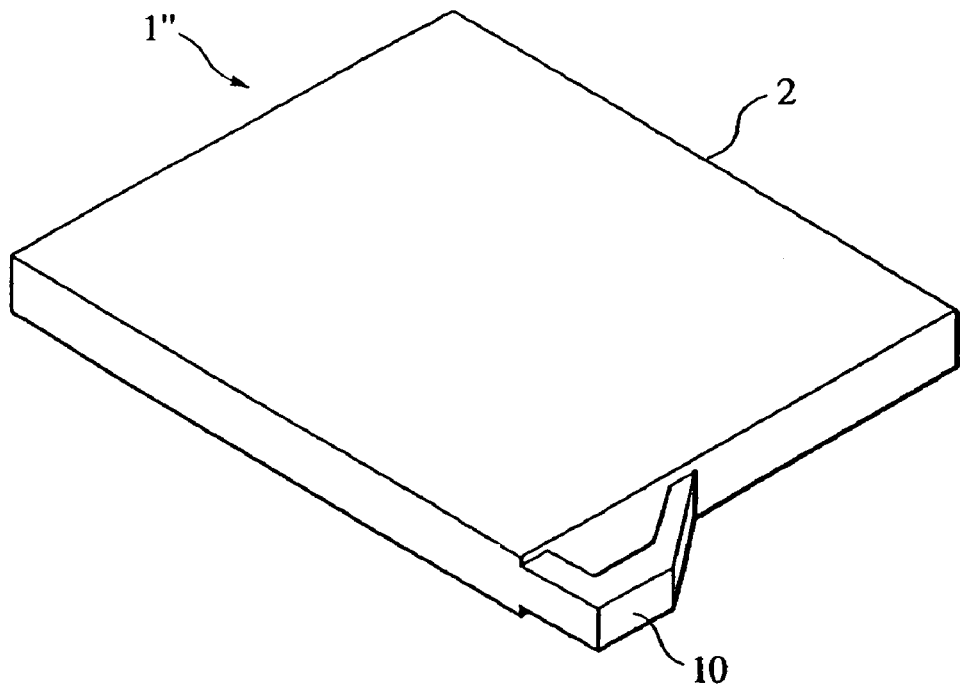
FIG. 14 is a perspective view of a conventional example of an electronic cassette.
Figure 15:
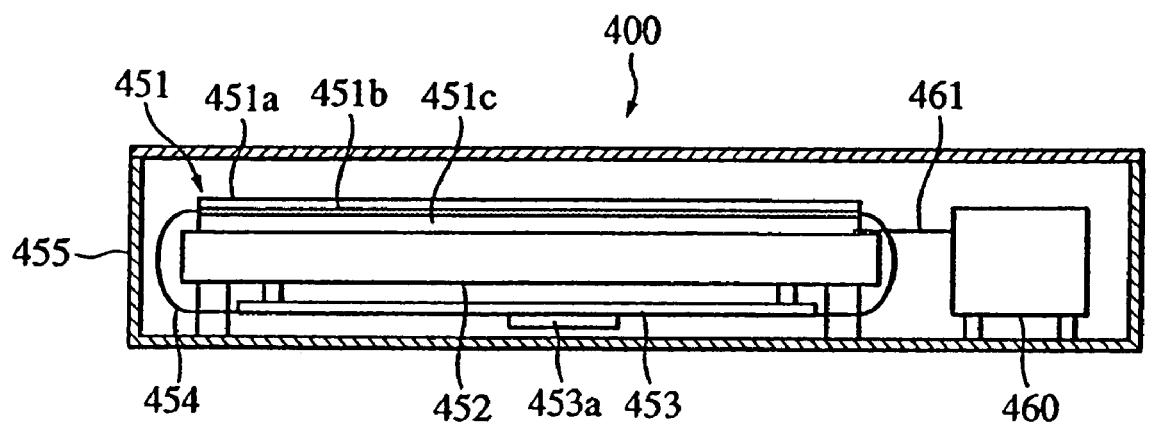
FIG. 15 is a perspective view of a conventional example of an electronic cassette.

Next, for clinical radiographing using a cassette, it is preferable that there is at least one side (housing side) such that the distance from the outer edge of the frame 201 up to the outer edge of the X-ray detection panel 202 is, for example, about 5 mm or less. By decreasing the distance from the outer edge of the frame 201 up to the outer edge of the X-ray detection panel 202, it becomes possible to take a photograph of a wide range of the shoulder when the photograph of the shoulder is taken from the above with the cassette being placed under the arm as described above with reference to FIG. 12 and possible to take a photograph of a wide range of the breast in a mammogram.

The following two selections are possible on the basis of the above conditions or prerequisites:

Selection 1: a driving circuit is disposed adjacent to one of the longer sides of the X-ray detection panel 202, no circuit is disposed in the other longer side, and the outer edge of the X-ray detection panel 202 is brought as close to the frame 201 as possible. An amplifier circuit is disposed in the vicinity of each of the two shorter sides of the X-ray detection panel 202, and each area formed by substantially dividing the X-ray detection panel 202 along the direction of the longer side into two portions is read by the amplifier circuit adjacent to each area.

Selection 2: an amplifier circuit is disposed adjacent to one of the longer sides of the X-ray detection panel 202, no circuit is disposed in the other longer side, and the outer edge of the X-ray detection panel 202 is brought as close to the frame 201 as possible. Each driving circuit is disposed in the vicinity of each of the two shorter sides of the X-ray detection panel 202, and each area formed by substantially dividing the X-ray detection panel 202 along the direction of the longer side into two portions is driven by the driving circuit adjacent to each area.

Which one of the selections 1 and 2 is preferable can be determined by estimating the degree of contribution to the S/N ratio in each case (which one can increase the S/N ratio) on the basis of the wiring length of each case. As a result of such an estimate, it could be seen that the selection 1 shown in FIG. 8 is the best selection. Furthermore, the correctness of the selection based on this estimate was demonstrated by an experiment.

Since the arrangement of the driving circuit and the amplifier circuit is determined in the manner described above, next, the arrangement of a power source which is a large component is considered. This power source supplies power to the X-ray detection panel 202, the amplifier circuit 203, the driving circuit 204, etc. Electromagnetic noise emitted from the power source is a major factor to be dealt with among various electromagnetic noises which exert an influence on the X-ray detection panel and each circuit. When disposing the power source, because an analog circuit has noise immunity lower than that of a digital circuit, in an electronic cassette in which a small size and lightweight are mandatory, it is preferable that the power source be disposed farther away from an analog amplifier circuit than the driving circuit which is a digital circuit. Therefore, as shown in FIG. 8, a power source 205 is preferably disposed around the driving circuit 204.

Next, the arrangement of the handle of the electronic cassette is considered. When the electronic cassette is carried by holding the handle, in order to minimizes interference of and/or impact on the electronic cassette, it is preferable that the length in the perpendicular (gravitational) direction when the electronic cassette is hung while holding the handle be short. Therefore, as shown in FIGS. 2 and 3, the handle is preferably disposed around the longer side of the X-ray detection panel. Furthermore, as shown in FIG. 8, since the handle cannot be disposed in a portion of the frame 201 to which the longer side of the X-ray detection panel 202 is brought as close as possible, the handle is provided around the other longer side of the X-ray detection panel 202. Furthermore, the handle is preferably a hole or a recess provided in the frame without protruding from the frame so as not to give a sense of incongruity to the subject in contact with the electronic cassette. Therefore, as shown in FIG. 8, it is most appropriate to provide a holding hole (handle section) 206 in the area of the frame 201 which does not interfere with the driving circuit 204 and a power source 205.

In the foregoing, the arrangement of the handle is determined on the basis of the preferable arrangement of the other components of the electronic cassette, and it can be seen that the determined arrangement of the handle is preferable from the following factors. That is, as has already been described, a portion of the body of the subject is sometimes photographed in a state in which the subject holds the electronic cassette by hand. In that case, since the oblong human body has many oblong portions, the electronic cassette is often used in radiography while being held oblong. Therefore, the arrangement of the handle (holding hole 206) around the longer side of the X-ray detection panel 202 makes it easy for the subject to hold the electronic cassette with the oblong arrangement, and thus is preferable.

In the above, an example in which the driving circuit is disposed only in the vicinity of one of the longer side of the X-ray detection panel 202 whose detection surface is formed rectangular is described. This is not an indispensable condition, and the construction may be formed in such a way that a driving circuit is disposed in the vicinity of each of the two longer sides of the X-ray detection panel 202, and each area formed by substantially dividing the X-ray detection panel 202 along the direction of the longer side into two portions is driven by the driving circuit adjacent to each area. Also, in this case, when electromagnetic noise which is generated by the power source is taken into consideration, an appropriate selection is still that the power source is provided around one of the longer sides of the X-ray detection panel 202 rather than the shorter sides. Furthermore, from the above-described reason and from the viewpoint of an efficient placement of the power source, provision of the handle section in the vicinity of the longer side where the power source is disposed is still advantageous.

As described above, in the fifth embodiment, as a result of disposing a handle on the longer side of the X-ray detection panel 202 whose detection surface is rectangularly formed, sensor driving with a high S/N ratio can be realized, and an adverse influence of electromagnetic noise which is generated by the power source can be reduced. In a case where a photograph is taken while the electronic cassette is held by the subject, in most cases, when, in particular, the electronic cassette is held oblong, it becomes easy to hold the electronic cassette by the subject by hand.

Figure 10:
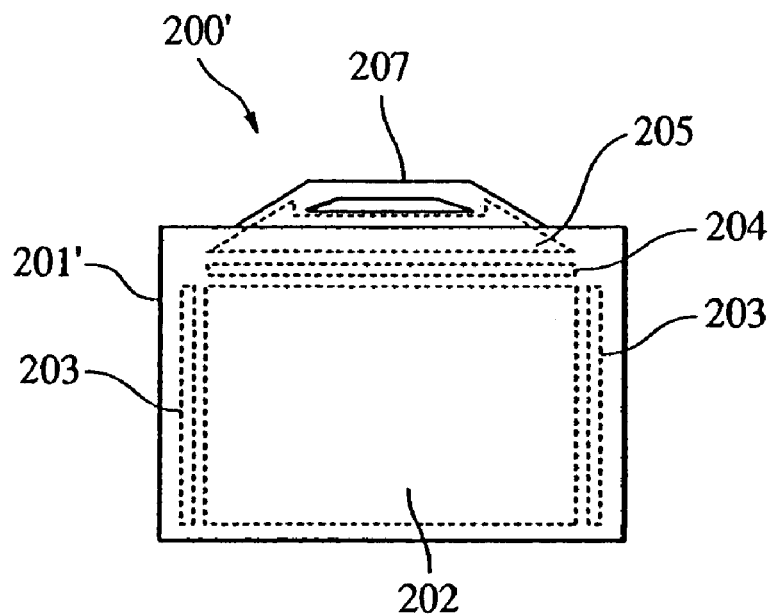
FIG. 10 is a plan view of a sixth embodiment of an electronic cassette according to the present invention.
Figure 11:
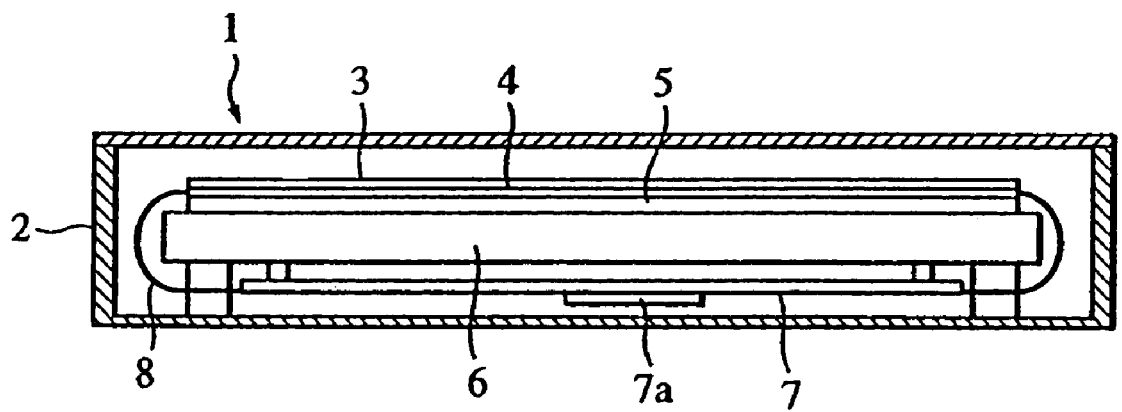
FIG. 11 is a sectional view of a conventional example of an electronic cassette.

FIG. 10 is a plan view of an electronic cassette 200' of a sixth embodiment of the present invention. Components which are the same as those of the fifth embodiment shown in FIG. 8 are given the same reference numerals, and accordingly, descriptions thereof are omitted. The difference is that, while a holding hole 206 is formed as a handle section by forming a hole or a recess in a frame 201 in the fifth embodiment, in this embodiment, a handle section 207 is mounted on one side of the frame 201' (housing) in the shape of a rectangular parallelepiped. This embodiment is similar to the fifth embodiment in that a handle section is disposed on the longer side of the X-ray detection panel 202 whose detection surface is formed rectangular. The same advantages in the efficient placement of components and noise reduction as those of the fifth embodiment can be obtained by the construction in such a way that power is supplied to the above-described electrical circuit, etc., within the frame 201' from the power source disposed inside such a handle section, or, as shown in FIG. 10, the frame 201' and the handle section 207 have a continuous internal space, and the power source is arranged over the inside of the frame 201' and the inside of the handle section. Of course, it is not indispensable that the entirety or a part of the power source be disposed inside the handle section 207, and the entirety of the power source may be disposed inside the frame 201' so as to be adjacent to, for example, a driving circuit 204.

As has thus been described, according to the radiographic apparatus of this embodiment, it is possible to provide a radiographic apparatus which solves the above-described problems, and which has high portability, wherein discomfort into a subject and decrease in the degree of freedom of radiographing are suppressed.

It is also possible to provide an electronic cassette to which a handle is appropriately attached by considering the properties specific to the electronic cassette.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A radiographic apparatus for detecting radiation, comprising:
a detection section having a rectangular detection surface and including photoelectric conversion elements that detect radiation;
an analog electrical circuit section arranged along a side of the detection surface for reading an electrical signal from the detection section;
a digital driving circuit section arranged along another side of the detection surface for driving the detection section;
a power source for supplying power to the detection section, the electrical circuit section and the driving circuit section; and
a housing that has a handle and contains the detection section, the electrical circuit section, the driving circuit section and the power source, wherein the driving circuit section, the power source and the handle are located along a longer side of the rectangular detection surface, wherein the electrical circuit section is arranged in two sections which are each arranged around a respective one of the two shorter sides of the detection surface, and each section of the electrical circuit section reads a partial detection area adjacent thereto, which area is defined by dividing the detection surface into two substantially equal parts in the longer side direction, and
wherein the detection section is included on a position where a distance between an outline of a longer side of the detection surface and an outline of the housing is shorter than a distance between an outline of the other longer side of the detection surface and the outline of the housing, and a handle is disposed on the side of the other longer side of the detection surface.

* * * * *